(12) United States Patent
Francon et al.

(10) Patent No.: US 8,557,253 B2
(45) Date of Patent: Oct. 15, 2013

(54) STABILIZING EXCIPIENT FOR INACTIVATED WHOLE VIRUS VACCINE

(75) Inventors: Alain Francon, Bessenay (FR); Michel Chevalier, Beaurepaire (FR); Nadege Moreno, Craponne (FR); Eric Calvosa, Haute Rivoire (FR); Sandrine Cigarini, Saint Genis les Ollieres (FR); Virginie Fabre, Lyons (FR)

(73) Assignee: Sanofi Pasteur SA, Lyons (FR)

( * ) Notice: Subject to any disclaimer, the term of this patent is extended or adjusted under 35 U.S.C. 154(b) by 188 days.

(21) Appl. No.: 12/899,492

(22) Filed: Oct. 6, 2010

(65) Prior Publication Data

US 2011/0081380 A1  Apr. 7, 2011

Related U.S. Application Data

(60) Provisional application No. 61/304,270, filed on Feb. 12, 2010.

(51) Int. Cl.
*A61K 39/205* (2006.01)
*A61K 47/00* (2006.01)
*C12N 7/02* (2006.01)

(52) U.S. Cl.
USPC .............. 424/224.1; 424/278.1; 435/239

(58) Field of Classification Search
None
See application file for complete search history.

(56) References Cited

U.S. PATENT DOCUMENTS 5,075,110 A  12/1991 Francon et al.
5,565,209 A * 10/1996 Rijke ........................ 424/423
6,008,036 A * 12/1999 Fanget et al. .............. 435/239
6,231,860 B1  5/2001 Fanget et al.
2010/0260798 A1  10/2010 Fabre et al.

FOREIGN PATENT DOCUMENTS

| CN | 101095950 | | 1/2008 |
| CN | 101095950 A | * | 1/2008 |
| WO | WO 2008/015419 | * | 2/2008 |
| WO | 2010/003670 | | 1/2010 |

OTHER PUBLICATIONS

Kallel et al (Journal of Biotechnology 95: 195-204, 2002).*
CN 101095950 A machine translation, 2008.*
CN 101095950 A Derwent abstract, 2008.*
Toriniwa et al., "Long-term stability of Vero cell-derived inactivated Japanese encephalitis vaccine prepared using serum-free medium," Vaccine, 26:3680-2689 (2008).
Kumar, et al., "Process Standardization for Optimal Virus Recovery and Removal of Substrate DNA and Bovine Serum Proteins in Vero Cell-Derived Rabies Vaccine," Journal of Bioscience and Bioengineering, vol. 94, No. 5, pp. 375-383, 2002.
Lang et al., Immunogenicity and Safety in Adults of a New Chromatographically Purified Vero-cell Rabies Vaccine (CPRV): A Randomized, Double-blind Trial With Purified Vero-cell Rabies Vaccine (PVRV), Biologicals (1998) 26, pp. 299-308.

* cited by examiner

*Primary Examiner* — Mary E Mosher
(74) *Attorney, Agent, or Firm* — McDonnell Boehnen Hulbert & Berghoff LLP

(57) ABSTRACT

The invention relates to a vaccine composition comprising:
a) inactivated whole virus, and
b) a stabilizing excipient which comprises:
 i. a buffer solution,
 ii. a mixture of essential and nonessential amino acids,
 iii. a disaccharide,
 iv. a polyol,
 v. a chelating agent,
 vi. urea or a urea derivative, and
 vii. a nonionic surfactant.

32 Claims, 2 Drawing Sheets ary of priority of U.S. pro-
STABILIZING EXCIPIENT FOR INACTIVATED WHOLE VIRUS VACCINE

CROSS-REFERENCE TO RELATED APPLICATIONS

This application claims the benefit of priority of U.S. provisional application 61/304,270, filed Feb. 12, 2010 and of French patent application no 09 04795, filed Oct. 7, 2009.

FIELD OF THE INVENTION

The subject of the present invention is a vaccine composition comprising inactivated whole virus and an excipient which stabilizes the vaccine composition, the composition of the excipient comprising a buffer solution, a mixture of essential and nonessential amino acids, a disaccharide, a polyol, a chelating agent, urea or a urea derivative and a nonionic surfactant. The present invention also relates to a process for preparing this vaccine composition and also to the composition of the excipient as such.

BACKGROUND OF THE INVENTION

In the viral vaccines field, a distinction is conventionally made between three types of viral vaccines: live virus vaccines, inactivated whole virus vaccines and subunit viral vaccines. These three types of vaccines differ by virtue of characteristics which are specific to them and which condition the composition of the excipients that are used to preserve them. Subunit vaccines containing a restricted number of viral antigens are generally easier to preserve than inactivated whole virus vaccines, for which it is sought to preserve the structural integrity of the viruses even if they are killed, or than live virus vaccines for which it is sought to also preserve the infectivity of the viruses. For each type of viral vaccine, suitable excipients have been prepared. For attenuated-virus vaccines, various stabilizing excipients have been prepared according to the preparation of attenuated viruses to be preserved. JP 57007423 describes an excipient comprising a disaccharide and on a polyalcohol in a phosphate buffer for stabilizing an attenuated strain of the measles virus. EP 065905 describes an excipient comprising one or more amino acids chosen from a group of eleven amino acids, lactose and sorbitol in a phosphate buffer for stabilizing an attenuated strain of the dengue virus. Finally, EP 0869814 describes a vaccine composition which comprises an attenuated strain of the chickenpox virus and a stabilizer containing sorbitol, mannitol, sucrose, dextran, an amino acid mixture, urea and EDTA.

In the inactivated virus vaccines field, ready-to-be administered vaccine compositions often contain proteins of animal origin, such as bovine or human albumin, gelatin or casein. Proteins are known to improve the preservation (stabilization) of these vaccines especially the vaccines that contain virus difficult to preserve. This is the case of vaccine compositions containing inactivated rabies virus. Frazatti-Gallina et al., in Vaccine (2004) Vol. 23, pp 511-517 emphasizes the importance of proteins in the stabilization of the rabies vaccine since the excipient contains albumin.

Nevertheless the presence of proteins in vaccines may represent a potential risk of disease transmission if their source is not rigorously controlled. They may also represent a potential risk of allergy, in particular when vaccines contain serum proteins, like albumin or derivatives thereof.

There therefore exists a need to find a stabilizing excipient, the composition of which does not contain protein, for stabilizing viral vaccines containing inactivated whole viruses, and in particular for stabilizing vaccines containing inactivated whole viruses that are difficult to preserve, such as rabies virus.

There also exists a need to find an excipient which is also suitable for stabilizing low-dose inactivated virus vaccines, i.e. vaccines which contain a small amount of total proteins in one effective dose of vaccine. This need is even greater for highly purified vaccines that contain very few residual protein impurities. Although the residual protein impurities can represent a potential risk of allergy, they can nevertheless contribute to stabilizing low-dose inactivated viral vaccines. They may prevent virus aggregation, virus degradation or virus adsorption that may cause a loss of efficacy of the vaccine.

To this effect, the subject of the present invention is:
A vaccine composition comprising:
a) a preparation of inactivated whole virus, and
b) a stabilizing excipient which comprises:
  i. a buffer solution,
  ii. a mixture of essential and nonessential amino acids,
  iii. a disaccharide,
  iv. a polyol,
  v. a chelating agent,
  vi. urea or a urea derivative, and
  vii. a nonionic surfactant.

Preferably, the inactivated whole virus is the rabies virus.

According to one aspect of the invention, the vaccine composition is free of serum protein.

According to another aspect, the vaccine composition is free of exogenous protein of animal origin. More preferably the vaccine composition is free of exogenous product of animal origin.

In yet another aspect, the virus proteins represent at least 70% of the total proteins present in the vaccine composition.

According to yet another aspect, the total protein concentration in the vaccine composition is ≤100 µg/ml. In one particular aspect, the amount of total proteins that is contained in one effective dose of the vaccine composition is ≤100 µg.

Typically, the amount of total proteins that is contained in one effective dose of the vaccine composition is between 1 µg and 50 µg.

In another aspect of the invention, the stabilizing excipient is free of protein, or of protein and of peptide or preferably free of protein, of peptide and of oligopeptide.

According to another aspect, the mixture of essential and nonessential amino acids contained in the vaccine composition comprises at least arginine or an arginine salt and glutamic acid or a glutamic acid salt.

Preferably, the amount of essential and nonessential amino acids contained in one effective dose of the vaccine composition is between 0.5 mg and 2.5 mg.

According to another aspect, the disaccharide that is contained in the excipient is maltose.

According to yet another aspect, the polyol that is contained in the excipient is sorbitol.

Preferably, the total amount of disaccharide and of polyol contained in one effective dose of the vaccine composition is between 10 mg and 50 mg.

In another aspect, the chelating agent that is contained in the excipient is EDTA or an EDTA salt.

Preferably, the amount of chelating agent contained in one effective dose of the vaccine composition is between 0.01 mg and 0.1 mg.

Preferably, the amount of urea or of urea derivative contained in one effective dose of the vaccine composition is between 0.3 mg and 1.5 mg.

In another aspect, the nonionic surfactant that is contained in the excipient is a poloxamer.

Preferably, the poloxamer is poloxamer 188.

Preferably, the amount of nonionic surfactant contained in one effective dose of the vaccine composition is between 0.001 mg and 0.5 mg.

According to another aspect, the pH of the vaccine composition is between 7.0 and 10.0, and preferably between 7.0 and 9.0.

In another aspect, the buffer solution is a phosphate buffer, a Tris buffer, a HEPES buffer, or a mixture thereof.

In one particular aspect, the buffer solution comprises a phosphate buffer, the molarity of which is between 10 and 100 mM.

A subject of the invention is also a method for preparing a vaccine composition containing a preparation of purified inactivated whole virus, the process comprising:
a. producing a whole virus preparation by harvesting the supernatant of a virus infected cell culture.
b. purifying then inactivating the whole virus preparation is purified and then inactivated or, alternatively inactivating and then purifying the whole virus preparation,
c. diluting the preparation of purified inactivated whole virus in a stabilizing excipient, the composition of said stabilizing excipient comprising:
   i. a buffer solution,
   ii. a mixture of essential and nonessential amino acids,
   iii. a disaccharide,
   iv. a polyol,
   v. a chelating agent,
   vi. urea or a urea derivative, and
   vii. a nonionic surfactant.

According to one preferred embodiment, the process is carried out without introducing any exogenous product of animal origin.

In another preferred embodiment of the process, the virus is the rabies virus.

In yet another embodiment, wherein the process further comprises dividing the vaccine composition into packaging devices and optionally freeze-drying the vaccine composition A subject of the invention is also a freeze-dried vaccine composition containing a preparation of purified inactivated whole virus, obtained according to a process of the invention.

A subject of the invention is also a stabilizing excipient for an inactivated whole virus vaccine, the composition of which comprises:
   i. a buffer solution,
   ii. a mixture of essential and nonessential amino acids,
   iii. a disaccharide,
   iv. a polyol,
   v. a chelating agent,
   vi. urea or a urea derivative, and
   vii. a nonionic surfactant.

Typically, the stabilizing excipient is free of protein, or of protein and of peptide, or alternatively free of protein, of peptide and of oligopeptide.

Preferably the stabilizing excipient is free of product of animal origin.

DETAILED DESCRIPTION OF THE INVENTION

Figure 1:
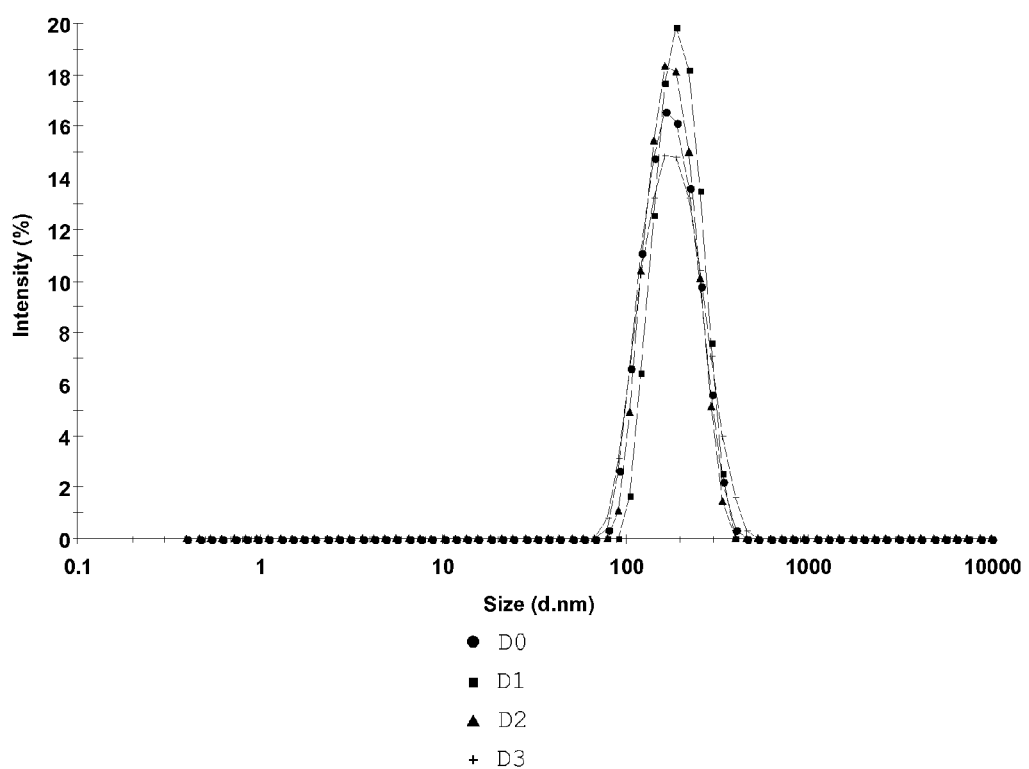
FIG. 1 is a superposition of the particle size distribution profiles analyzed by Dynamic Light Scattering of a vaccine composition in which the composition of the stabilizing excipient is F04+0.001% poloxamer 188 during a cycle of three successive thawings and refreezings (● D0: before freezing, ■ D1: after the first thawing; ▲ D2 (after the second thawing and + D3 (after the third thawing)

The vaccine composition according to the invention comprises whole inactivated virus (or a preparation of whole inactivated viruses) and a stabilizing excipient, the composition of which comprises a buffer, a mixture of essential and nonessential amino acids, a disaccharide, a polyol, a chelating agent, urea or a urea derivative, and a nonionic surfactant. The composition of the excipient advantageously replaces the prior art excipients that contain in their composition a protein. Particularly advantageously, it stabilizes vaccine compositions that are difficult to preserve, and most particularly vaccine compositions that contain the rabies virus as inactivated whole virus without it being necessary to add thereto a protein.

The vaccine composition according to the invention is at the same time stable in liquid form, in frozen liquid form or in freeze-dried form, thereby offering great flexibility for use.

The stabilizing excipient according to the invention preserves the biological activity of the vaccine composition over time whatever its form (frozen, liquid, or freeze dried). The storage temperature of the frozen vaccine compositions is generally ≤−35° C.; it is between +2° C. and +8° C. for vaccine compositions in liquid form, and about +5° C. for vaccine compositions in freeze-dried form. Interestingly, It also preserves the biological activity as well as the physical integrity of the virus in the vaccine compositions when they are stored in bad (stressed) conditions, for instance when the vaccine compositions in liquid form are stored at +37° C. or when the frozen vaccine compositions are repeatedly thawed and refrozen.

The biological activity of the virus in the vaccine composition is assessed by measuring, over time and under well-designed storage conditions, the amount of an immunogen component of the virus, which is essential for inducing protective immunity against the virus, and/or by testing the efficacy of the vaccine composition in a challenge assay in an animal model officially accepted when such assay is available. In the case of a vaccine composition containing inactivated whole rabies virus, the stability of the vaccine composition is evaluated by measuring, over time (or after repeated thawings and refreezings), the virus titer given by the level of the glycoprotein G in a nondenatured form and/or by testing the efficacy of the vaccine composition by means of the official NIH test. To assess the glycoprotein G level, a sandwich ELISA method, which recognizes at least one, preferably two conformational epitopes of the glycoprotein G, as it is described in example 1, may be used. When an ELISA which recognizes two conformational G protein epitopes is carried out, a rabies virus-neutralizing antibody which recognizes a conformational epitope located on the antigenic site II of the glycoprotein G (Journal of Clinical Investigation (1989), Vol. 84, pp 971 to 975) is normally used as capture antibody, and a neutralizing antibody which recognizes a conformational epitope located on the antigenic site III of the G protein (Biologicals (2003), Vol. 31, pp 9 to 16) is normally used as revealing antibody. The results of the ELISA are expressed in international units since a standard which has been calibrated with respect to the NIBSC international reference is normally used as reference. A surface Plasmon resonance assay (Biacore Technology) considered as an improvement of the classical ELISA may also be used for the quantification of the virus.

The stabilizing excipient according to the invention also preserves the physical integrity of the viral particles. It prevents the formation of aggregates and/or the structural modification of the viral particles over time. This can be monitored with the Zetasizer Nano ZS apparatus (Malvern Instrument) that detects aggregates and provides the size distribution profile of the viral particles in the vaccine composition.

The inactivated whole virus (or the preparation of inactivated whole viruses) is in the form of whole viral particles which have been inactivated, generally by chemical treatment with formol, formaldehyde or with β-propiolactone. Other inactivation methods, such as the one which is described in WO 2005/093049, may also be used. The whole virus preparations usually contain enveloped inactivated whole viruses since they are often more difficult to preserve than non enveloped viruses and they often require the use of specific excipient compositions in order to preserve them. They are in particular preparations of inactivated whole Japanese encephalitis virus. Particularly preferably, the inactivated whole virus preparations contain rabies virus.

The term "virus" encompasses indistinctly virus and viruses.

The virus preparations originate from harvests which are generally in the form of samplings of culture supernatants from cells infected with the virus. Conventional media supplemented with serum of animal origin can be used to produce the stock of cells and/or to infect the cells. Advantageously, the media which are used to produce the cells and/or the virus are free of any serum protein, or even preferably are free of any product of animal origin. The proteins which are possibly present in these media are generally low-molecular-weight proteins (≤10 KD) or rather polypeptides at very low concentrations (≤15 µg/ml), thereby reducing the risks of allergy accordingly. This is the case, for example, of the media sold under the names VP SFM (InVitrogen), Opti Pro™ serum-free (InVitrogen), Episerf (InVitrogen), Ex-cell® MDCK (Sigma-Aldrich), Ex-Cell™ Vero (SAFC biosciences), MP-BHK® serum free (MP Biomedicals), SFC-10 BHK express serum free (Promo cell), SFC-20 BHK express protein free (Promo cell), HyQ PF Vero (Hyclone Ref. SH30352.02), Hyclone SFM4 Megavir, MDSS2 medium (Axcell biotechnology), Iscove's modified DMEM medium (Hyclone), Ham's nutritive media (Ham's-F10, Ham's-F12), Leibovitz L-15 medium (Hyclone). For example, the harvests of rabies virus are obtained from a batch of Vero cells that have been produced and infected using a cell culture medium and a virus infection medium that are preferably free of serum, free of any protein of animal origin, and even free of any product of animal origin, such as the VP SFM medium.

Typically, the preparation of whole inactivated virus contained in the vaccine composition is highly purified. The virus which comes from the harvest is normally purified and then inactivated or, conversely, inactivated and then purified. When all the virus production and purification steps are carried out without using serum protein, and without using any exogenous product of animal origin, the biological safety of the vaccine composition according to the invention is maximum; the risk of allergy as well as the risk of disease transmission (like BSE) are optimally reduced. The term "protein or product of animal origin" is intended to mean a protein or a product for which the production process comprises at least one step in which a material originating from an animal or from a human is used. The term "exogenous protein or exogenous product" is intended to mean any protein or any product which is used in one of the steps of the virus production and/or purification process. For example, the proteins or the products which are possibly present in the composition of the culture media, and enzymes such as trypsin or benzonase which are used during the virus production and/or purification steps are exogenous proteins. The exogenous proteins or exogenous products are of animal origin when their manufacturing process comprises at least one step in which a material originating from an animal or from a human is used. The exogenous proteins or exogenous products are of non animal origin when they are produced by other means, for example using a plant material, by chemical synthesis or by genetic recombination using yeasts, bacteria or plants. The proteins or the products originating from the cells which are used for virus production are, on the other hand, "endogenous proteins or endogenous products" since they are produced (or released) at the same time as the viruses.

In the context of the present invention, particularly effective purification processes which result in the production of highly purified virus preparations may advantageously be carried out. By way of example, mention is made of the virus purification process which comprises anion exchange chromatography followed by cation exchange chromatography and finished off with metal-chelation affinity chromatography, which is described in WO 97/06243. To purify and inactivate the rabies viruses from infected cell culture supernatants, a method of choice consists in using a process which is described in the patent application filed in France on Apr. 14, 2009, under number 0952310, which comprises a cation exchange chromatography step on a chromatography support comprising a polymethacrylate matrix onto which sulfoisobutyl groups have been grafted, a benzonase treatment step, a sucrose gradient ultracentrifugation step, an inactivation step with β-propiolactone and an ultrafiltration step in a buffer solution. The preparations of whole and inactivated rabies virus obtained are highly purified but they are more difficult to preserve (stabilize) since there are fewer residual protein impurities. This difficulty is even greater when the preparation contain small amounts of virus.

By virtue of the composition of the excipient, the vaccine composition according to the invention remains stable even when the total protein concentration is ≤100 µg/ml, ≤80 µg/ml, ≤50 µg/ml or even ≤20 µg/ml. In general, the total protein concentration is between 1 and 50 µg/ml and the virus proteins represent at least 70% of the total proteins, preferably at least 80% of the total proteins, and particularly preferably at least 90% of the total proteins that are present in the vaccine composition according to the invention. In one effective dose of vaccine, this usually represents an amount of total proteins ≤100 µg or ≤50 µg or even ≤20 µg. By way of indication, the residual amount of DNA is, for its part, <100 pg per effective dose of vaccine. The expression "effective dose of a vaccine" or "effective dose of vaccine composition" (and the like) are intended to mean the amount of the composition according to the invention that contains an amount of inactivated virus that is capable of inducing protective immunity in humans or animals after administration according to the route of immunization and the immunization protocol that are recommended in the context of a primary vaccination or of a booster vaccination. In the case of vaccination against the rabies virus, the efficacy of the rabies vaccine is determined by means of the NIH test described in the WHO rabies monograph (WHO Technical Series Report 941-January 2007)

which is the official test accepted by the WHO. One dose of inactivated rabies vaccine is effective when it contains at least 2.5 IU according to this test. The administration of this dose intramuscularly in humans according to the vaccination or sero-vaccination protocols normally recommended induces the development of protective immunity against rabies.

The "total proteins" correspond to all the proteins that are present in the vaccine composition. They are essentially represented by the viral proteins, but also by the residual proteins that have not been eliminated during the purification process such as the cell proteins, the proteins from the cell and viral culture media, and the proteins which have been possibly introduced during the purification process (for example, benzonase in the case of the rabies virus purification process as mentioned above) are also taken into account even if they are considered as residual proteins. The Bradford method is generally used to quantify the total proteins. To quantify the proportion of viral proteins among the total proteins, polyacrylamide gel electrophoresis under denaturing and reducing conditions is carried out on a sample of the vaccine composition, followed by staining with coomassie blue and densitometric analysis of the electrophoretic profile. In the case of a vaccine composition containing inactivated whole rabies virus, the viral proteins represented by the envelope glycoprotein G, the nucleoprotein N, the phosphoprotein P, the matrix protein M and the RNA-dependent RNA polymerase L are easily identifiable among the other proteins on a polyacrylamide gel electrophoresis. The amount of total proteins contained in one effective dose of the vaccine composition according to the invention is generally between 1 µg and 50 µg, preferably between 2 µg and 20 µg. Particularly preferably, at least 70%, at least 75%, at least 80%, at least 85%, or even at least 90% of the total proteins are viral proteins. The excipient according to the invention is especially advantageous since it stabilizes vaccine compositions difficult to preserve, like vaccine compositions containing inactivated whole rabies virus, and in which one effective vaccine dose contains:

an amount of viral proteins which represents at least 70% of the total proteins and/or
  less than 100 µg of total proteins, most commonly an amount of total proteins of between 1 µg and 50 µg, preferably between 2 µg and 20 µg.

The composition of the excipient according to the invention is preferably free of any protein, free of any peptide and even free of any oligopeptide and usually does not contain any product of animal origin, so as to reduce as much as possible the biological safety issues and/or the risks of allergy that may be associated with their use.

In the context of the present invention, the meaning of the following expression "the stabilizing excipient is free of protein" shall be understood as a stabilizing excipient, the composition of which is free of biological macromolecule comprising more than 50 amino acids linked together by peptide bonds.

The following expression "the stabilizing excipient is free of protein and of peptide" shall be understood as a stabilizing excipient, the composition of which is free of biological macromolecule comprising more than 20 amino acids linked together by peptide bonds.

The following expression "the stabilizing excipient is free of protein, of peptide and of oligo peptide" shall be understood as a stabilizing excipient, the composition of which is free of biological molecule comprising amino acids linked together by one or several peptide bonds. For example a dipeptide that contains two amino acids linked by one peptide bond is excluded from the composition of a stabilizing excipient free of protein, of peptide and of oligo peptide.

The mixture of amino acids which is part of the composition of the excipient comprises at least one essential amino acid from all the essential amino acids represented by cystine, tyrosine, arginine, histidine, isoleucine, leucine, lysine, methionine, phenylalanine, threonine, tryptophan and valine, and at least one nonessential amino acid from all the nonessential amino acids represented by aspartic acid, glutamic acid, alanine, asparagine, glutamine, glycine, proline and serine. The amino acids with an acid function may be in the acid form or in the form of salts. This is likewise the case for the basic amino acids.

Preferably, the excipient according to the invention contains at least arginine or an arginine salt, such as arginine hydrochloride, and glutamic acid or a glutamic acid salt, such as sodium glutamate. Ultimately, the mixture of amino acids preferably comprises from 1 to 12 essential amino acids among which there is at least arginine or a salt thereof and from 1 to 8 nonessential amino acids among which there is at least glutamic acid or a salt thereof. Arginin and glutamic acid or their salt thereof are the main components of the mixture of essential and non essential amino acids since they usually represent by weight at least two-thirds of the total amount of essential and non essential amino acids. The total amino acid concentration in the vaccine composition is generally ≤20 g/l, and is more often between 2 g/l and 10 g/l. In one effective dose of the vaccine composition according to the invention, this represents a total amount of amino acids of ≤5 mg, preferably an amount which is between 0.5 mg and 2.5 mg, and particularly preferably between 0.8 mg and 1.8 mg. The ratio of the amount of arginine (in hydrochloride form) to the total amount of amino acids contained in the excipient is in general greater than 0.5, while the ratio of the amount of glutamic acid (in sodium glutamate form) to the total amount of amino acids contained in the excipient is less than 0.5.

The excipient according to the invention also contains a disaccharide. Disaccharides which originate from material of animal origin, such as milk, are not used. As disaccharide suitable for the subject of the invention, mention is made of sucrose, maltose or trehalose, but maltose is preferably used, alone or in combination with another disaccharide such as sucrose. The polyol which is also included in the composition of the excipient is also preferably of nonanimal origin. It is principally a hexyl such as sorbitol and/or mannitol. Sorbitol is preferably used since mannitol has the drawback of crystallizing when the vaccine composition according to the invention is in a freeze-dried form. The total concentration of disaccharide and of polyol in the vaccine composition is generally between 30 g/l and 100 g/l. Preferably, the excipient according to the invention contains maltose and sorbitol. In one effective dose of the vaccine composition, this normally corresponds to an amount of between 10 mg and 50 mg, and preferably to an amount of between 20 mg and 25 mg. The amount of maltose generally represents at least 70% of the total amount of maltose and sorbitol.

The chelating agent is also one of the components of the excipient according to the invention. It is principally EDTA (ethylenediaminetetraacetic acid) or a salt thereof ($Na^+$, $K^+$, etc.). The EDTA or EDTA-salt concentration in the vaccine composition is generally between 0.02 g/l and 0.5 g/l, and preferably between 0.02 g/l and 0.2 g/l. In one effective dose of the vaccine composition, this normally corresponds to an amount of between 0.01 mg and 0.1 mg, preferably between 0.01 mg and 0.05 mg, and particularly preferably between 0.01 mg and 0.04 mg of EDTA or of EDTA salt.

Urea or a urea derivative, such as allylurea, acetamide, methyl carbamate or butyl carbamate, is also a part of the composition of the excipient. Preferably, the vaccine composition contains urea at a concentration of generally between 1 g and 10 g/l, preferably at a concentration of between 1 g and 5 g/l. In one effective dose of the vaccine composition, this normally corresponds to an amount of between 0.3 mg and 3 mg, preferably between 0.3 mg and 1.5 mg, and particularly preferably between 0.4 mg and 1.2 mg of urea.

The excipient according to the invention also comprises a nonionic surfactant which contributes to stabilizing the vaccine composition. Without wishing to be bound by the theory it helps to maintain the biological activity of the virus, the physical integrity of viral particles by avoiding the formation of aggregates or the structural degradation of viruses. It may also prevent adsorption of the virus onto the walls of the packaging, in particular when the walls are made of glass or plastic. A nonionic surfactant suitable for the subject of the invention is produced from a raw material of nonanimal origin and is pharmaceutically compatible with parenteral administration of the product. As a class of nonionic surfactants particularly suitable for the subject of the invention, mention is made of poloxamers, which are "block copolymers" of ethylene oxide and of propylene oxide having the chemical formula $HO(C_2H_4O)_a(C_3H_6O)_b(C_2H_4O)_aH$ according to which a denotes the number of ethylene oxide units and b denotes the number of propylene oxide units. The poloxamers have a molecular weight generally ranging from 1000 to 16000. The poloxamers which are of particular interest have a molecular weight of between 5000 and 15500. The poloxamers are sold in particular under the trade name Pluronic®, among which is Pluronic® F68, or poloxamer 188, which denotes a poloxamer in solid form at ambient temperature, the molecular weight of the polyoxypropylene part of which is approximately 1750 and the polyoxyethylene part of which represents approximately 80% of the total weight of the molecule. Among the poloxamers, poloxamer 188 (Pluronic® F68) is especially advised. Possibly, a sorbitan ester, in particular polyoxyethylenated sorbitan ester sold under the trade name Tween®, like Tween® 20 (polyoxyethylene (20) sorbitan monolaurate or polysorbate 20) or Tween® 80 (polyoxyethylene (20) sorbitan monooleate or polysorbate 80) can also be used.

The nonionic surfactant suitable for the subject of the invention is used within a very low concentration range that preserves the structure and the size of the inactivated viral particles. At too high concentration, the surfactant can dissociate or modify the structure of the viral particles in particular enveloped viruses, which may adversely affect the immunogenicity of the vaccine composition.

When Pluronic® F68 is used as surfactant, the concentration in the vaccine composition is generally less than 1 g/l, preferably between 0.005 g/l and 1 g/l and particularly preferably between 0.01 g/l and 0.1 g/l; In this concentration range, there is no adjuvant effect on the immune system induced by the surfactant. In one effective dose of the vaccine composition, this normally corresponds to an amount between 0.001 mg and 0.5 mg, and preferably between 0.003 mg and 0.03 mg. Preferably, the vaccine composition according to the invention contains Pluronic® F68 as non ionic surfactant, or possibly contains a mixture of Pluronic® F68 and Tween® 20.

The buffer solution of the excipient according to the invention is chosen such that the pH of the vaccine composition is between 7.0 and 10.0, preferably between 7.0 and 9.0, and particularly preferably between 7.8 and 8.3. Within this pH range, the physical thermostability of the inactivated virus particles, and especially the physical thermostability of the rabies virus particles, is at a maximum. The phase diagram studies show that it is necessary to heat the rabies virus preparation to a temperature of at least 60° C. in order to observe rabies virus particle aggregation when the pH is between 7.3 and 8.3, whereas, at a pH<6.0, considerable aggregation is observed at ambient temperature. The buffer solution is usually a phosphate buffer, a Tris buffer or a HEPES buffer, or a mixture thereof. The concentration of the buffer solution is generally between 10 mM and 100 mM. Preferably, the composition of the excipient comprises a phosphate buffer, the molarity of which is normally between 10 mM and 100 mM, or a mixture of a phosphate buffer and a Tris buffer in the same range of molarity.

A vaccine composition particularly preferred according to the invention comprises:
 A preparation of inactivated whole rabies viruses and a stabilizing excipient comprising:
  A phosphate buffer;
  A mixture of essential and non essential amino acids containing at least arginin or a salt thereof and glutamic acid or a salt thereof;
  Maltose;
  Sorbitol;
  EDTA or a salt thereof;
  Urea;
  Poloxamer 188;
wherein the pH of the vaccine composition is between 7.3 and 8.3

Possibly, Tween 20 may also be incorporated as additional surfactant in this vaccine composition. This vaccine composition is advantageously free of any serum protein and free of any exogenous product of animal origin and the preparation of inactivated whole rabies viruses is highly purified (i.e. the proportion of viral proteins among the total proteins in the vaccine composition is at least 70%, and preferably at least 80%). Poloxamer concentration in the vaccine composition is <1 g/l and preferably between 0.01 g/l and 0.1 g/l; The concentration of phosphate buffer is generally between 10 and 100 mM. arginin and glutamic acid or their salt thereof are the main components of the mixture of essential and non essential amino acids and represent by weight at least two-thirds of the total amount of essential and non essential amino acids. The mixture of essential and non essential amino acids is usually between 2 and 10 g/l, the total concentration of maltose and sorbitol is usually between 50 and 100 g/l, the concentration of EDTA or its salt thereof is usually between 0.02 and 0.2 g/l and urea is usually between 1 and 5 g/l. The concentration in total proteins in the vaccine composition is usually between 5 and 50 µg/ml. In one effective dose of the vaccine composition, it represents usually an amount of essential and non essential amino acids between 0.5 mg and 2.5 mg, an amount of maltose and sorbitol between 10 and 50 mg, an amount of EDTA or of its salt thereof between 0.01 mg and 0.1 mg, an amount of urea between 0.3 and 1.5 mg, an amount of poloxamer 188 between 0.001 and 0.5 mg, and an amount of total proteins between 2 and 20 µg.

The process for preparing a vaccine composition according to the invention besides the steps of production, purification and inactivation of the virus preparation comprises a step in which the stabilizing excipient is introduced into the preparation of purified inactivated whole viruses and a step in which the resulting composition is divided up into packaging devices. Usually, the virus preparation is diluted into the stabilizing excipient before being divided up into packaging devices.

The vaccine composition according to the invention can be under the form of a bulk. In that case, the inactivated whole virus concentration is higher than that which is in the vaccine composition once divided up, but the composition of the stabilizing excipient is the same. The distribution step of the vaccine composition into the packaging devices is carried out by thawing the bulk that is subsequently diluted into the stabilizing excipient until the desired viral concentration is obtained. A final bulk product is obtained, which is subsequently divided up into the packaging devices. In order to guarantee the sterility of the vaccine composition, a step of sterilizing filtration, for example through a filtering membrane of 0.2 µm, may also be incorporated, before the dividing-up step.

The bulk is generally obtained by diafiltration of the purified and inactivated virus preparation obtained at the end of the purification process in a buffer solution that is generally the same as the buffer solution of the stabilizing excipient. For instance, if the buffer of the stabilizing excipient is a 50 mM phosphate buffer, a 50 mM phosphate buffer will be used during the diafiltration step. If it is desired to increase the concentration of virus, the diafiltration step is preceded by an ultrafiltration step. The ultrafiltration membrane has a low cut-off threshold, of generally between 5 kDa and 100 kDa, preferably between 8 kDa and 50 kDa, and particularly preferably around 10 kDa so as to obtain maximum retention of the virus in the retentate and to remove the salts which may have a negative impact on the freeze-drying process. The retentate containing the purified virus preparation is mixed in a second step with the stabilizing excipient. A bulk having the composition of the vaccine composition according to the invention is then obtained. A buffer having the same composition as the stabilizing excipient may also be used during the diafiltration step to obtain in one step the bulk.

The process for preparing a vaccine composition according to the invention containing purified inactivated whole rabies virus comprises the following steps: a preparation of whole rabies virus is obtained by harvesting the supernatant of a Vero cell culture that has been infected with rabies virus using cell-culture and viral-infection media that are preferably free of any serum protein and of any product of animal origin, for instance using VP SFM medium. The purification and the inactivation of the virus are subsequently carried out using in particular the process as described in the patent application filed in France on Apr. 14, 2009, under number 0952310, which comprises a step of cation exchange chromatography for which the support preferably comprises a polymethacrylate-based matrix onto which sulfo isobutyl groups are grafted, a treatment with a recombinant benzonase, a sucrose gradient ultracentrifugation step, and an inactivation step with β-propiolactone. The inactivated whole rabies virus preparation is highly purified, free of any serum protein and free of any exogenous product of animal origin. The residual DNA content is <100 pg/ml and the viral proteins represent at least 70% of the total proteins. A bulk is then prepared according to the embodiments of the previous paragraph. It is usually stored at a temperature below −35° C. The bulk is then diluted to the desired viral concentration in the stabilizing excipient according to the invention before being divided into the packaging devices.

The vaccine composition is normally divided up into the packaging devices in a volume which is generally between 0.1 and 1 ml such that the composition, once divided up, contains at least one effective dose of vaccine in each packaging.

The packaging devices used for dividing up the final bulk product are normally in the form of bottles (made of glass or plastic) or of syringes, but any other packaging device compatible with vaccination practice may also be used.

The size particle analysis of vaccine compositions according to the invention containing purified rabies virus by means of the Zetasizer Nano ZS instrument (Malvern Instrument) which measures the Brownian motion of the particles by dynamic light scattering shows the existence of a single homogenous population of viral particles of between 100 nm and 300 nm, with an average value of 180 nm, which corresponds to the mean size of the wild type rabies virus. Neither aggregates, nor modifications of the distribution profile of the virus particle size are observed during the storage of these vaccine compositions.

The vaccine composition according to the invention is stable for at least 3 months at a temperature of 2-8° C. and 1 month at 23-27° C. under a liquid form. It may also be stored for at least 12 months, and preferably for at least 24 months, under a frozen form at a temperature of ≤−35° C. (see example 3). Finally, the product divided up can be readily freeze-dried using a conventional freeze-drying process. By virtue of the composition of the excipient according to the invention, there is no significant loss of virus during the freeze-drying step. When the vaccine composition according to the invention contains inactivated whole rabies virus, a freeze-drying method comprises freezing the composition at a temperature of less than −40° C. and then desiccating the product in two stages, the first desiccation being carried out at a temperature in the region of −15° C. at 80 µbar and the secondary desiccation being carried out at a temperature in the region of +40° C. at 80 µbar. The freeze-dried divided-up product has a residual water content of ≤3% and is stable at a temperature of 2-8° C. for at least 18 months (see example 3). In fact, the rabies virus vaccine composition as described in the invention proves to be as stable as a prior art vaccine composition sold under the name VeroraB™ which contains an amount of total proteins per vaccine dose that is at least 100 times greater than that which may be encountered in this viral composition, which generally contains an amount of total proteins within the range of 1 µg to 50 µg per one effective dose. Moreover, the composition of the excipient according to the invention also makes it possible to store the vaccine composition on a long-term basis in various forms, even though the preferred storage form is the freeze-dried form.

The vaccine composition can be administered directly to the individual to be vaccinated when it is stored in liquid form, or after thawing if it is stored frozen. When it is in a freeze-dried form, the freeze-dried material is taken up extemporaneously in a diluent which is normally a saline solution, for instance a hypotonic sodium chloride solution. The diluent may also contain a surfactant at very low concentration, the chemical structure of which is pharmaceutically compatible with parenteral use. The surfactant is normally Tween® 20, Tween® 80 or Pluronic® F68, which is used at a concentration that is too low to exert any adjuvant action. The concentration of the surfactant in the diluent is generally ≤0.1% (w/w).

When the vaccine is under a freeze-dried form, it is normally under the form of a kit with two packagings, the first (generally in the form of a bottle) contains the freeze-dried vaccine composition, the second (generally in the form of a bottle or of a syringe) contains the diluent. A "bypass" syringe, in which the vaccine composition is in the lower part of the syringe while the upper part contains the diluent, may also be used.

Finally, a subject of the invention is a stabilizing excipient for an inactivated whole virus vaccine, in particular for an inactivated whole rabies virus vaccine, which comprises:
a. a buffer solution,
b. a mixture of essential and nonessential amino acids,
c. a disaccharide,
d. a polyol,
e. a chelating agent,
f. urea or a urea derivative, and
g. a nonionic surfactant.

Preferably, the excipient is free of any protein, preferably of any peptide and of any protein, and even more preferably of any protein, of any peptide and of any oligopeptide. Particularly preferably, the excipient is free of product of animal origin.

The present invention will be understood more clearly in the light of the following examples which serve to illustrate the invention without, however, limiting the content.

Example 1

Influence of the Excipient on the Stability of a Vaccine Composition Containing Purified and Inactivated Whole Rabies Virus in the Bulk Form 1.1 Preparation of the Bulk The rabies virus was produced on Vero cells using a serum-free viral infection medium. The cells of the Vero line were adapted to serum-free-medium culture conditions as described in application WO 01/40443. They were then transferred into a biogenerator containing cytodex 1 microcarriers in VP SFM medium (Invitrogen). After a culture period of 3 to 4 days at 37° C., maintaining a pH of approximately 7.2±0.2 and an oxygen saturation of 25%±10% and subjecting the medium to mild agitation, cells were infected with rabies virus at a multiplicity of infection of 0.01 using a serum-free viral infection medium containing VP SFM medium (Invitrogen). The infected-cell culture supernatents were harvested at days D7 (H1), D11 (H2) and D15 (H3). After each harvest, new viral infection medium was reintroduced. The culture supernatants containing the infectious virus were clarified using two successive filtrations: the first using an 8 µm polypropylene prefilter (Sartopure PP2, Sartorius), which removes the few microcarriers drawn up during the harvesting, the Vero cells and the large cell debris; the second using a PES filter, composed of the combination of two filters, at 0.8 µm and 0.45 µm (Sartopore 2, Sartorius), which removes the aggregates. The amount of rabies virus present in the clarified harvest was determined on the basis of measuring the amount of glycoprotein G (gpG), performed by ELISA in the following way:

Approximately 0.12 µg/100 µl of a solution of an anti-gpG monoclonal antibody 1112-1 (the characteristics of which are described in Journal of Clinical Investigation (1989), volume 84, pages 971 to 975), diluted beforehand in a "coating" buffer (0.2M carbonate/bicarbonate buffer, pH 9.6), was distributed in the wells of an ELISA microplate. After overnight incubation in a cold room, followed by several washes with a washing buffer (phosphate buffer supplemented with 0.05% Tween 20), 100 µl of a saturation buffer (phosphate buffer supplemented with bovine serum albumin at 1%) were distributed into each well. After incubation for one hour at 37° C., followed by several washes, a range of dilutions was prepared for each test sample, in a dilution buffer (phosphate buffer supplemented with Tween 20 at 0.05% and with serum albumin at 0.1%). In parallel, in each microplate, a range of dilutions of a reference standard, which was calibrated with respect to the NIBSC international reference (for example PISRAV), was prepared. After a further incubation for one hour at 37° C., followed by several washes, 100 µl of a solution of an anti-gpG mouse monoclonal antibody D1 (the characteristics of which are described in Biologicals (2003), volume 31, pages 9 to 16), which was biotinylated and used after dilution to 1/5000 in the dilution buffer, were distributed into each well. The plates were left for 1 hour at 37° C. and then washed several times, before distributing, into each of the wells, 100 µl of a solution of peroxidase-coupled streptavidin (Southern Biotechnology Associates) diluted beforehand to 1/15000 in the dilution buffer. After a further incubation for one hour at 37° C., followed by several washes, 100 µl of a solution of a 0.05M citrate buffer, pH 5, containing the developing substrate (O-phenylenediamine), were distributed into each well. After a period of incubation of 30 minutes at ambient temperature in the dark, the developing reaction was stopped by adding 50 µl/well of a 2N solution of $H_2SO_4$. The spectrophotometric reading of the microplates was carried out at two wavelengths (492 nm and 620 nm). The optical density measured is the difference between the two readings so as to take into account the absorption by the plastic. The relative activity was calculated using the parallel line analysis according to the recommendations of the European Pharmacopea. The rabies virus titer of the test sample is based on the determination of the concentration of rabies virus glycoprotein G, which is expressed in IU/ml relative to the reference.

After also having verified the conductivity and the pH of the clarified liquid, the equivalent of approximately 50 IU of glycoprotein G (measured by ELISA), per ml of support, were loaded onto the Fractogel® EMD $SO_3^-$ chromatographic support (Merck), pre-equilibrated with 20 mM Tris buffer containing 150 mM NaCl, pH=7.5. The chromatographic support was then washed with the equilibration buffer and then the rabies virus was eluted in 20 mM Tris buffer containing 600 mM NaCl, pH=7.5, with recovery of the viral peak in an independent fraction. An ultrafiltration step was then carried out on a PES Medium Screen 100 KD membrane (Pall) followed by diafiltration in 20 mM Tris buffer containing 150 mM NaCl, pH=7.5. A solution of $MgCl_2$ was added such that the concentration in the medium was 2 mM. The benzonase treatment was carried out by adding 15 U/ml of crude harvest to the reaction medium and leaving the reaction medium for 2 hours at laboratory temperature. The ultracentrifugation step was carried out on 34-60% sucrose cushions with a Ti 45 rotor at 21000 rpm for 2 h at +5° C. The fractions of the gradient containing the purified virus were collected, combined, and then diluted in 50 mM phosphate buffer containing 150 mM NaCl, pH=7.5, such that the final volume of the purified-virus suspension was approximately 12.5 times smaller than the volume of the clarified harvest. The purified-virus suspension was then inactivated by treatment with β-propiolactone followed by inactivation of the β-propiolactone by heating at a temperature of approximately 37° C. for 2 hours. The preparation of purified and inactivated viruses was concentrated 6-fold by ultrafiltration on a 10 kDa membrane (Omega medium screen, Pall) followed by diafiltration in 50 mM phosphate buffer containing 150 mM NaCl, pH 7.5. The rabies virus preparation obtained is in the form of a concentrated bulk, the titer of which, based on the determination of the glycoprotein G concentration, was approximately 80 IU/ml. An aliquot of the bulk was then dialyzed against each of the four excipients (F01 to F04) to be tested, the compositions of which were the following.

1.2 Composition of the Excipients Tested

F01: 50 mM phosphate buffer, 150 mM NaCl, maltose (5% w/w), pH=8.0

F02: 50 mM phosphate buffer, maltose (5% w/w), pH=8.0

F03: 50 mM phosphate buffer, maltose (5% w/w) poloxamer 188 (BASF) (0.001% w/w), pH=8.0

F04: 489 PM buffer, pH=8.0, the composition of which is the following:

| Components | Volume/Amount |
|---|---|
| Essential amino acids | 40 ml |
| Nonessential amino acids | 40 ml |
| Sorbitol (Roquette) | 20 g |
| Arginine hydrochloride (Jerafrance) | 4 g |
| EDTA (Prolabo) | 0.148 g |
| Sodium glutamate (SAFC) | 1.6 g |
| $Na_2HPO_4 \cdot 2H_2O$ | 8.428 g |
| $NaHPO_4 \cdot 2H_2O$ | 0.413 g |
| Maltose (Hayashibara) | 50 g |
| Urea | 4 g |
| Adjustment to pH = 8.0 with 10N sodium hydroxide | |
| Demineralized water qs | 1000 ml |

The solution of essential amino acids was prepared by dissolving the content of a bottle containing 111.5 g of essential amino acids (Gibco, reference 074-90680N, batch number 14773) in 5 liters of injection-grade water acidified with 100 ml of 12N HCl (Prolabo).

The solution of nonessential amino acids was prepared by dissolving the content of a bottle containing 40.7 g of nonessential amino acids (Gibco, reference 074-90681N, batch number 14775) in 5 liters of injection-grade water.

1.3 Tests Carried Out on the Four Formulations of the Bulk

Once dialyzed, four bulks were obtained, each one of them being distinguished by the composition of its excipient (F01, F02, F03 or F04). The stability of these four formulations (vaccine compositions) was evaluated over time at various storage temperatures: −70° C., +5° C. and at +37° C. by measuring the glycoprotein G titer (expressed in IU/ml) at regular intervals. The results obtained are represented in tables I to III and are expressed in IU/ml.

TABLE I

Stability of the four formulations of the bulk stored at +37° C.

| | Time (weeks) | | |
|---|---|---|---|
| | 0 | 1 | 2 |
| F01* | 41.25** | 30.21 | 17.51 |
| F02 | 60.41 | 23.15 | 5.12 |
| F03 | 60.29 | 23.16 | 5.2 |
| F04 | 57.26 | 52.37 | 52.68 |

TABLE II

Stability of the four formulations of the bulk stored at +5° C.

| | Time (weeks) | | | |
|---|---|---|---|---|
| | 0 | 3 | 12 | 24 |
| F01* | 41.25** | 39.71 | 45.56 | 38.55 |
| F02 | 60.41 | 53.29 | 42.27 | 38.92 |

TABLE II-continued

Stability of the four formulations of the bulk stored at +5° C.

| | Time (weeks) | | | |
|---|---|---|---|---|
| | 0 | 3 | 12 | 24 |
| F03 | 60.29 | 52.64 | 47.75 | 41.33 |
| F04 | 57.26 | 62.19 | 61.06 | 61.32 |

TABLE III

Stability of the four formulations of the bulk stored at −70° C.

| | Time (weeks) | | | |
|---|---|---|---|---|
| | 0 | 3 | 12 | 24 |
| F01* | 41.25** | 33.81 | 37.61 | 27.59 |
| F02 | 60.41 | 53.52 | 53.06 | 53.62 |
| F03 | 60.29 | 57.87 | 60.15 | 56.46 |
| F04 | 57.26 | 57.48 | 59.92 | 56.56 |

*F01, F02, F03 and F04 refer to the composition of the excipient in which each of the bulks was formulated.
**in IU/ml These results show that the F04 excipient is the one which most successfully stabilizes the preparation of purified and inactivated whole rabies viruses, in particular when the storage temperature increases. This also shows that an excipient comprising a sugar (maltose) and a nonionic surfactant such as poloxamer 188 in a solution buffered at a pH of 8.0 is not sufficient to stabilize a rabies virus preparation.

Example 2

Role of the Surfactant in the Stabilization of Vaccine Compositions Containing Purified Whole Rabies Virus 2.1 Preparation of the Vaccine Compositions A suspension of purified whole viruses was obtained by using the same process as the one used in example 1. After the ultracentrifugation step, the purified virus preparation was in a highly concentrated form. The protein concentration was measured by the Bradford assay and found to be of 7 mg/ml. The virus preparation was then divided up in 3 polypropylene recipients and diluted in 3 different excipients to be tested for their stabilizing effect, so that the final protein concentration in each of the test excipient was lowered to 10 μg/ml (dilution factor: 1/700). The composition of the 3 test excipients only differed by their poloxamer 188 content but all the 3 test excipients contain the 489 PM Buffer, pH=8.0, the composition of which is described in example 1. The excipient without poloxamer 188 had the same composition as the F04 excipient described in example 1. The two other test excipients were supplemented respectively with 0.01 g/l poloxamer 188 (the so called "F04+0.01% poloxamer 188) and with 0.1 g/l poloxamer 188 (The so called "F04+0.1% poloxamer 188).

2.2 Stability Studies and Results

The stability of the 3 rabies vaccine compositions was evaluated in experiments where successive freeze-thawings were carried out according to the following protocol:

The 3 vaccine compositions were frozen at −70° C. on the same day (day D0). Each of the 3 compositions was then subjected to three successive thawings at +5° C. followed by refreezing at −70° C. within 7 to 14 hours following the thawing, on days 1, 2 and 3 (respectively D1, D2 and D3). The stability of the vaccine compositions after each thawing was assessed by virus titration. This was measured by the determination of the total viral protein concentration based on the virus capture through its antigenic component, glycoprotein G, using Surface Plasmon Resonance assay (BIAcore). The particle size distribution profile was also analyzed by Dynamic light Scatttering (DLS).

To carry out the Surface Plasmon Resonance assay, the monoclonal antibody D1– was covalently linked to the sensor chip, using the BIAcore amine coupling kit according to the manufacturer's instructions (amine coupling kit, BR-1000-50). Then, 30 μl of the sample to be tested was automatically injected for three minutes. The interaction between the rabies virus in the sample and the monoclonal antibody covalently linked to the sensor chip induced a modification of the refractive index at the sensor ship surface and therefore modified the recorded signal (RU). The results were recorded in arbitrary units (ΔRU) and were compared with the results obtained with a calibration range of a standard that contains a known amount of purified rabies virus. The ΔRU observed for each test sample was then converted into total viral protein concentration in the test sample based on the calibration curve obtained with the standard. Quadruplicate analyses were made for each sample tested. After each measure, the sensor ship was washed by two successive injections of 10 μl of Glycine buffer (10 mM, pH=1.5). The results obtained for each vaccine composition tested are represented in table IV, under below, and are expressed in μg/ml of viral proteins.

TABLE IV

Study of the stability of the 3 vaccine compositions during a cycle of three successive thawings and refreezings

| Stabilizer | D0 | D1 | D2 | D3 | Titer loss |
|---|---|---|---|---|---|
| F04 | 11* (0.5)** | 3.4 (0.4) | 2.1 (0.3) | 1.4 (0.3) | 88% |
| F04 + 0.001% poloxamer 188 | 14.8 (0.3) | 11.2 (0.5) | 10.8 (0.5) | 9.9 (0.6) | 33% |
| F04 + 0.01% Poloxamer 188 | 18.9 (0.0) | 15.7 (0.3) | 15.2 (0.4) | 14.7 (0.4) | 23% |

*mean total viral protein titer of quadruplicate measures of the same sample in μg/ml
**in bracket is indicated the standard deviation calculated from the quadruplicate measures carried out on the same sample.

The results clearly shows that the stabilizer F04 in absence of poloxamer 188 is unable to preserve efficiently a rabies virus preparation since the titer loss is 88% between the titer observed just before freezing (D0) and the titer observed after the third thawing (D3). On the other hand as soon as the stabilizer F04 is slightly supplemented with the non ionic surfactant poloxamer 188, the titer loss is strongly lowered (it is of 33% when F04 is supplemented with 0.001% poloxamer 188 and of 23% when F04 is supplemented with 0.01% poloxamer 188. These results clearly show that the stabilizer shall contain both the components of the 489 PM buffer F04 and poloxamer 188 to stabilize efficiently a rabies virus vaccine composition.

Figure 2:
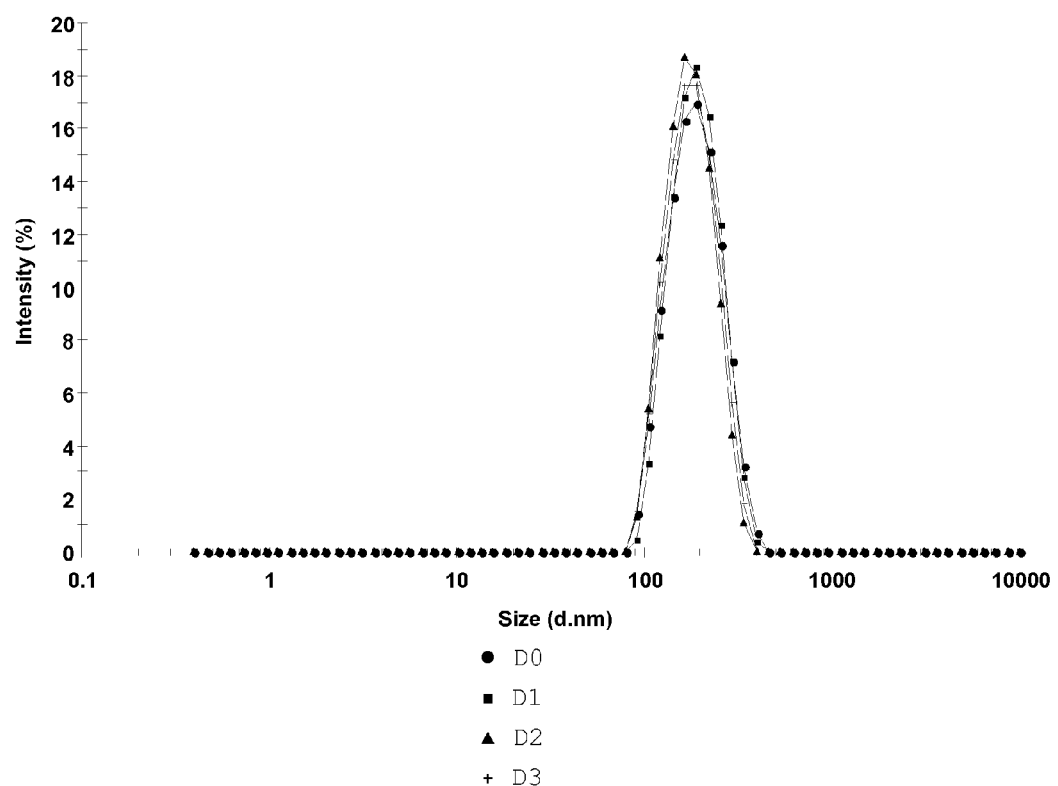
FIG. 2 is a superposition of the particle size distribution profiles analyzed by Dynamic Light Scattering of a vaccine composition in which the composition of the stabilizing excipient is F04+0.01% poloxamer 188 during a cycle of three successive thawings and refreezings (● D0: before freezing, ■ D1: after the first thawing; ▲ D2 (after the second thawing and + D3 (after the third thawing)

The particle size distribution profile of each of the 3 vaccine compositions was also tested after each thawing by Dynamic light scattering using a Zetasizer Nano Zs apparatus (Malvern Instruments). A sample of 450 μl was introduced in a disposable polystyrene bowl and submitted to a monochromatic laser radiation (laser HeNe, λ=632.8 nm). The signal that was recorded by the apparatus corresponded to the fluctuations of the scattered light resulting from the Brownien motion of the particles. The recorded data were then treated by software. The results were finally represented under the form of a distribution curve of the particle size in the test sample. In the two figures are respectively shown a superposition of the four distribution curves obtained with a rabies vaccine composition in which the stabilizer is F04+0.001% poloxamer 188, on Days 0 (before freezing), 1, 2, and on day 3 (D1, D2 and D3) (FIG. 1) and with a rabies vaccine composition in which the stabilizer is F04+0.01% poloxamer 188 (FIG. 2). These two figures clearly show that:

1) the distribution curves of the particle size are unimodal and have a Gaussian profile centred on about 180 nm. This means that the population of viral particles in the rabies vaccine composition stabilized either with F04+0.001% poloxamer 188 or with F04+0.01% poloxamer 188 is homogeneous, does not contain aggregates, and comprises a population of whole rabies virus similar to the wild type rabies virus population and, 2) the distribution curves of the particle size are not modified when the rabies virus vaccine compositions are thawed and refreezed several times.

Therefore, the presence of a non ionic surfactant like poloxamer 188 in the excipient preserves the physical integrity of the rabies virus population when the vaccine composition is stored in stressed conditions.

2.3 Stability Studies on Freeze-Dried Vaccine Compositions 2.3.1 Preparation of the Freeze-Dried Vaccine Compositions A bulk was first prepared from a purified inactivated whole virus preparation obtained after having implemented the same process as that used in example 1.

After the viral inactivation step, the preparation of purified and inactivated rabies viruses was diafiltered through a 10 KDa membrane (Omega medium screen, Pall) using an excipient called 488 TM which was prepared from a medium 488, the composition of which is the following (see table below):

| Components | Volume/Amount |
|---|---|
| Mixture of essential amino acids and nonessential amino acids | 200 ml |
| Sorbitol (Roquette) | 50 g |
| Arginine hydrochloride (Jerafrance) | 10 g |
| EDTA (Prolabo) | 0.37 g |
| Sodium glutamate (SAFC) | 4 g |
| Urea | 10 g |
| Tris $NaH_2PO_4 \cdot 2H_2O$ (SAFC) | 2.42 g |
| Demineralized water qs | 1000 ml |
| 6N hydrochloric acid (Sanofi) qs | pH = 8.0 |

The mixture of essential and nonessential amino acids was prepared by mixing 2.5 liters of the solution of essential amino acids prepared according to example 1 with 2.5 liters of the solution of nonessential amino acids prepared according to example 1, and adjusting the pH to approximately 7.2 with a 30% sodium hydroxide solution.

The composition of the 488 TM excipient is the following:

| Components | Volume/Amount |
|---|---|
| Medium 488 | 400 ml |
| Maltose (Hayashibara) | 50 g |
| Tris NaH$_2$PO$_4$•2H$_2$O (SAFC) | 1.45 g |
| Demineralized water qs | 1000 ml |
| 6N hydrochloric acid (Sanofi) qs | pH = 8.0 |

The vaccine preparation obtained was in the form of a bulk into the 488 TM excipient, the viral titer of which, based on the determination of the glycoprotein G concentration by ELISA, was about 12 IU/ml. The bulk was then stored under a frozen form at −70° C. until the time at which the freeze-dried vaccine compositions were prepared.

Just before the freeze-drying step, an aliquot of the bulk was thawed and diluted so as to bring the final glycoprotein G titer back to about 8 IU/ml, using:
- either the F'04 excipient, the composition of which contains one volume of the 488 TM excipient for three volumes of 50 mM phosphate buffer, 50 g/l maltose pH=8.0,
- or the F'05 excipient, which is identical to the F'04 excipient, but to which poloxamer 188 has been added at a final concentration of 0.01 g/l.

The two vaccine compositions were then divided up into freeze-drying bottles in a proportion of 0.4 ml/bottle, and then a conventional freeze-drying cycle was carried out, comprising a freezing phase at less than −40° C. followed by two successive desiccation phases, the first desiccation phase being carried out at a temperature of approximately −15° C. at a pressure of approximately 80 μbar and the second at a temperature of approximately +40° C. at a pressure of approximately 80 μbar.

Each freeze-drying bottle contains one dose of the vaccine composition to be tested. The freeze-dried vaccine compositions obtained differed only by virtue of the presence or absence of poloxamer 188 depending on whether the bulk was diluted in the F'04 or F'05 excipient.

The composition of the excipient contained in one dose of the freeze-dried vaccine composition that has resulted from the dilution of the bulk into the F'05 excipient, is given below.

| Component | Amount in mg/dose |
|---|---|
| Mixture of essential and nonessential amino acids | 0.12 |
| Poloxamer 188 | 0.004 |
| Maltose | 20.00 |
| Arginine hydrochloride | 0.41 |
| Sorbitol | 2.05 |
| Disodium EDTA | 0.01 |
| Urea | 0.41 |
| Sodium glutamate | 0.16 |
| Na$_2$HPO$_4$•2H$_2$O | 2.53 |
| NaH$_2$PO$_4$•2H$_2$O | 0.12 |
| Tris | 0.24 |
| HCl | qs |
| NaOH | qs |

2.3.2 Efficacy of the Freeze-Dried Vaccine Compositions

The two freeze dried vaccine compositions that were prepared using two different excipients, were then tested for their efficacy in the official NIH activity test.

"The efficacy" of the two freeze-dried vaccine compositions was analyzed either immediately after freeze-drying (D0), or after storage for one week at 45° C., or also after storage for one month at 37° C. The NIH test officially recognized was used to determine the number of IUs contained in each of the doses of the vaccine compositions tested. If the number of IUs is ≥2.5 IU, the vaccine dose tested is effective. The NIH test was carried out each time in "duplicate" for each of the conditions tested by randomly sampling two freeze-dried bottles in the batch of bottles that were prepared and stored under the same conditions and by performing the NIH test on each of the bottles. The protocol used corresponds to monograph 0216 of the European Pharmacopea. This is a challenge test carried out in mice, based on the comparison between the protection conferred by the dose of vaccine tested, with that conferred by an amount of a reference rabies vaccine preparation. The reference rabies vaccine preparation is calibrated in international units (IU). The international unit (IU) is the activity contained in a given amount of an international standard. The equivalence in IU of the international standard has been established by the WHO. After having checked that the internal control parameters were valid, the number of IUs contained in the dose of vaccine tested was calculated from the values of the 50% protective dose obtained for each dose of vaccine composition tested and for the reference preparation (calibrated in IUs).

The results obtained are represented in table V below.

TABLE V

Efficacy of the freeze-dried vaccine compositions according to the composition of the freeze-drying excipient used and the storage conditions

| | Storage time (in days) and storage temperature of the freeze-dried composition | | |
|---|---|---|---|
| | D0/+4° C. | D7/+45° C. | D30/+37° C. |
| F'04 | 0.8* (0.4; 1.8)** | 0.9 (0.4; 2.1) | NT |
| F'05 | 6.1 (1.6; 41.3) | 2.8 (0.9; 7.9) | 3.5 (1.4; 8.7) |

*mean value expressed in IU obtained (all the groups of mice that were challenged contain 16 mice)
**represents the extreme values obtained expressed in IU
NT: not tested These results are in accordance with the previous results discussed in paragraph 2.2 and show that poloxamer shall be included in the composition of the excipient to be used for preserving freeze-dried vaccine compositions. Indeed, only the freeze-dried vaccine compositions stabilized with the F'05 excipient (which contains poloxamer) contain an effective dose of vaccine since the number of IU is greater than 2.5 IU. These vaccine compositions remain stable since their efficacy is not affected over time under the temperature conditions tested.

To sum up, the results presented in example 2 shows that rabies vaccine compositions can be well preserved with a stabilizing excipient, the composition of which comprises a phosphate buffer, a mixture of essential and nonessential amino acids, a sugar like maltose, a polyol like sorbitol, EDTA, urea, in combination with a nonionic surfactant like poloxamer 188. Moreover and quite interestingly, the positive stabilizing effect of poloxamer 188 is observed at a very low concentration that is too low to activate the immune system or to act as an adjuvant of the immune response.

Example 3

Study of the Stability of Vaccine Compositions Containing Purified and Inactivated Whole Rabies Virus Examples 1 and 2 having shown the need of combining components of an excipient that comprises a mixture of essential and nonessential amino acids, maltose, sorbitol, EDTA, urea in a phosphate-based and/or Tris-based buffered solution with poloxamer 188 to preserve rabies virus preparations the purpose of these studies was to confirm that such excipient was also effective in preserving rabies virus vaccine compositions in various forms (liquid, frozen, freeze-dried) at various storage temperatures (+37° C., +25° C., +5° C., −70° C.) over a long period of time. These studies were performed on several rabies vaccine compositions that were stored either under a bulk form at a temperature ≤−35° C., or under a final bulk product form at +5° C., or at +25° C. or under the form of freeze-dried unit doses at different storage temperatures (+5° C., +25° C. or +37° C.).

3.1 Stability Studies of a Rabies Vaccine Composition Stored Under a Frozen Bulk Form The rabies vaccine used in the preparation of the bulk batches was prepared according to the method as described in example 1. After the final inactivation step, the preparation of purified and inactivated whole virus was diafiltered through a 10 KDa membrane using a 50 mM phosphate buffer as diafiltration buffer. In a second step, one volume of retentate was mixed with one volume of stabilizing excipient. The composition of the stabilizing excipient was the same as the PM 489 buffer described in example 1, except that the amount of each of the component was two fold higher and that it also contained poloxamer 188 at a final concentration of 0.02 g/l, pH≈8.0. A bulk having a total protein content of about 50 µg/ml among which more than 70% are rabies virus proteins and having less than 100 pg/ml of residual DNA, was obtained.

The stability of the bulk over time after storage in polypropylene vials at −35° C. and at −70° C. was studied by measuring the glycoprotein G titer every 3 months. The results obtained are given in table VI below.

TABLE VI

Stability of a bulk batch stored at −35° C. or at −70° C.

| Storage temperature | T0 | T0 + 3 months | T0 + 6 months | T0 + 9 months | T0 + 12 months |
|---|---|---|---|---|---|
| −35° C. | 20.4* | 20.84 | 24.4 | 24.3 | 22.4 |
| −70° C. | 21.3 | NT | 22.4 | 22.8 | 21.8 |

*titer expressed in IU/ml
NT: not tested

After a 12 month storage period at −35° C. or at −70° C., no degradation of glycoprotein G, which is the major rabies virus antigen, is observed, thereby confirming the good stability of the vaccine composition under a frozen bulk form. Furthermore, the viral particle size distribution analysis carried out by DLS after storage for 12 months at −35° C. or at −70° C. shows that the profiles retain a Gaussian appearance centered on 180 nm like the profiles observed in FIG. 1 and FIG. 2. The lack of any "fragmentation" in the profiles means that the particle population remains homogeneous and does not contain viral aggregates. These results also show that the population of rabies virus particles is not modified over time. To conclude, there is neither degradation nor aggregation of viral particles in the vaccine composition over time.

3.2 Stability Studies of a Rabies Vaccine Composition Stored Under a Liquid Final Bulk Product Form 3 batches under the form of a liquid final bulk product were produced from several batches of bulk after dilution into 489 PM buffer (composition described in example 1) supplemented with poloxamer 188 at a final concentration of 0.01 g/l, pH≈8.0. They contained less than 100 pg/ml of residual DNA (measured by quantitative PCR). The total protein content was about 15 µg/ml (measured according to the Bradford technique), and more than 70% of the total proteins were represented by viral proteins after densitometric analysis of the Polyacrylamide Gel electrophoresis.

The stability of the final bulk product batches stored in glass vials at +5° C. and at +25° C. was studied by periodically measuring the glycoprotein G titer over a 3 month period of time when the storage temperature was +5° C. and over a 30 day period of time when the storage temperature was +25° C. The results obtained are given in tables VII and VIII below.

TABLE VII

Stability over time of 3 final bulk product batches stored at +5° C.

| Batch Number | T0 | T0 + 1 month | T0 + 2 months | T0 + 3 months |
|---|---|---|---|---|
| N° 1 | 10.5 | 12.0 | 8.6 | 10.8 |
| N° 2 | 11.1 | 10.7 | 9.3 | 11.9 |
| N° 3 | 13.9 | 11.1 | 11.6 | 11.2 |

TABLE VIII

Stability over time of 3 final bulk product batches stored at +25° C.

| Batch Number | T0 | T0 + 15 days | T0 + 30 days |
|---|---|---|---|
| N° 1 | 12.0 | 10.9 | 10.9 |
| N° 2 | 10.7 | 11.4 | 10.1 |
| N° 3 | 11.1 | 12.0 | 11.5 |

These results shows that there is no degradation of glycoprotein G over the time periods considered, thereby confirming the good stability of the vaccine compositions when there are stored under a liquid form for at least a 3 month period of time and at least a 30 day period of time when the storage temperatures are respectively +5° C. and +25° C.

3.3 Stability Studies of Rabies Vaccine Compositions Stored Under a Freeze-Dried Form Two batches of rabies virus vaccine compositions under freeze-dried form (LL1 and LL2) were prepared from the batches of final bulk products described in example 3.2 which were divided up into glass freeze-drying bottles in a proportion of 0.3 ml/bottle, and then freeze-dried according to the following process: the freezing was carried out at a temperature ≤−40° C., the primary desiccation phase at a temperature about −15° C. at a pressure of approximately 80 µbar until complete sublimation of the ice, and the secondary desiccation phase at about +40° C. at a pressure of approximately 80 µbar until the residual water content is ≤3% in the freeze-dried materials. The viral titer loss was evaluated during the freeze-drying step and found to be <5%. The composition of the excipient contained in one freeze-dried dose of the vaccine composition is the following:

| component | Amount in mg/dose |
|---|---|
| Mixture of essential and nonessential amino acids | 0.37 |
| Poloxamer 188 | 0.003 |
| Maltose | 15.00 |
| Arginine hydrochloride | 1.20 |
| Sorbitol | 6.00 |
| Disodium EDTA | 0.04 |
| Urea | 1.2 |
| Sodium glutamate | 0.15 |
| $Na_2HPO_4 \cdot 2H_2O$ | 2.53 |
| $NaH_2PO_4 \cdot 2H_2O$ | 0.12 |
| HCl | qs |
| NaOH | qs |

The freeze-dried unit doses obtained had a homogenous white appearance. The pH of the rabies virus suspension after the freeze-dried materials were taken up with 0.5 ml of a 0.4% sodium chloride solution, was in a range of 7.8±0.5. The stability of the freeze-dried unit doses resulting from the two batches was studied over time at three storage temperatures: 35-39° C., 23-27° C. and 2-8° C.; the appearance of the freeze-dried materials before and after reconstitution was checked, the residual water content was measured, the pH and the viral titer were also controlled as well as the efficacy of the doses in the NIH test. The first dilution of the dilution ranges which were prepared in order to test the freeze-dried compositions in the NIH test after they have been taken up in sodium chloride, was made in a 0.9% sodium chloride solution containing 2 g/l of human albumin. The viral titers were assessed on the basis of the measurement of glycoprotein G by ELISA and expressed in IU/ml.

The results of the tests about the appearance of the freeze-dried materials, about their residual water contents, and about pH were all conformed to the specifities (i.e. a homogenous white appearance for the freeze-dried material, a colorless clear solution after reconstitution in hypotonic physiological saline, a residual water content <3%) irrespective of the storage temperature and time. The pH remained very stable in the range of 7.8±0.5 during the overall study period.

The results relating to the viral titers and to the efficacy of the freeze-dried vaccine compositions are given in tables IX to XI.

TABLE IX

Stability over time of 2 batches of freeze-dried vaccine compositions stored at +5° C.

| Batch | Test | T0 | 1 M | 3 M | 6 M | 9 M | 12 M | 18 M |
|---|---|---|---|---|---|---|---|---|
| LL1 | Virus titer | 7.1* | 7.7 | 7.8 | 7.9 | 7.3 | 8.8 | 7.8 |
| | Efficacy | 3.4** (1.9-6.1) | ND | ND | 6.3 (3.6-10.9) | ND | 6.0 (3.5-10.3) | 6.3 (3.3-11.9) |
| LL2 | Virus titer | 6.1 | 6.6 | 6.7 | 6.5 | 6.9 | 6.4 | ND |
| | efficacy | 4.7 (2.6-8.6) | ND | ND | 7.9 (4.5-14) | ND | 6.7 (3.7-12.) | ND |

TABLE X

Stability over time of 2 batches of freeze-dried vaccine compositions stored at +25° C.

| Batch | Test | T0 | 1 M | 3 M | 6 M |
|---|---|---|---|---|---|
| LL1 | Virus titer | 7.7 | 7.1 | 7.8 | 6.9 |
| | Efficacy | ND | ND | ND | 7.0 (4.0-12.2) |

TABLE X-continued

Stability over time of 2 batches of freeze-dried vaccine compositions stored at +25° C.

| Batch | Test | T0 | 1 M | 3 M | 6 M |
|---|---|---|---|---|---|
| LL2 | Virus titer | 6.6 | 6.1 | 6.0 | 6.2 |
| | efficacy | ND | 6.8 (3.9-11.8) | ND | 8.9 (5.1-15.6) |

TABLE XI

Stability over time of 2 batches of freeze-dried vaccine compositions stored at +37° C.

| Batch | Test | T0 | 1 M | 3 M | 6 M |
|---|---|---|---|---|---|
| LL1 | Virus titer | 7.7 | 7.5 | 10.1 | 10.3 |
| | Efficacy | ND | 7.1 (3.1-16.1) | ND | 8.6 (5.0-14.9) |
| LL2 | Virus titer | 6.6 | 7.2 | 7.5 | 7.7 |
| | efficacy | ND | 8.8 (3.7-20.9) | ND | 6.2 (3.5-11.3) |

M: means "month(s)"
ND means "not done"
*in IU/ml
**mean value expressed in IU and in bracket are mentioned the extreme values obtained expressed in IU.

The overall results confirm that the freeze-dried vaccine compositions stored in the tested conditions are very stable.

In conclusion, all the stability tests carried out both on the bulk batches, the final bulk product batches and on the freeze-dried vaccine batches confirm that these vaccine compositions are stable over time under the different storage conditions tested. It confirms that an excipient, the composition of which comprises a phosphate buffer, a mixture of essential and nonessential amino acids, a sugar like maltose, a polyol like sorbitol, EDTA, urea, in combination with a nonionic surfactant like poloxamer 188 is very effective in preserving rabies virus vaccine compositions in various forms (liquid, frozen, freeze-dried) at various temperatures of storage (+37° C., +25° C., +5° C., −70° C.) over a long period of time

What is claimed is:
1. A vaccine composition comprising:
a) a preparation of inactivated whole rabies virus, and
b) a stabilizing excipient which comprises:
  i) a buffer solution,
  ii) a mixture of essential and nonessential amino acids,
  iii) a disaccharide,
  iv) a polyol, v) a chelating agent,
vi) urea or a urea derivative, and
vii) a nonionic surfactant.

2. The composition as claimed in claim 1, wherein the vaccine composition is free of serum protein.

3. The composition as claimed in claim 2, wherein the vaccine composition is free of exogenous protein of animal origin.

4. The composition as claimed in claim 3, wherein the vaccine composition is free of exogenous product of animal origin.

5. The composition as claimed in claim 4, wherein the virus proteins represent at least 70% of the total proteins present in the vaccine composition.

6. The composition as claimed in claim 5, wherein the total protein concentration in the vaccine composition is ≤100 µg/ml.

7. The composition as claimed in claim 6, wherein the amount of total proteins that is contained in one effective dose of the vaccine composition is ≤100 µg.

8. The composition as claimed in claim 7, wherein the amount of total proteins that is contained in one effective dose of the vaccine composition is between 1 µg and 50 µg.

9. The composition as claimed in claim 1, wherein the stabilizing excipient is free of protein, or of protein and of peptide.

10. The composition as claimed in claim 1, wherein the mixture of essential and nonessential amino acids comprises at least arginine or an arginine salt and glutamic acid or a glutamic acid salt.

11. The composition as claimed in claim 1, wherein the amount of essential and nonessential amino acids contained in one effective dose of the vaccine composition is between 0.5 mg and 2.5 mg.

12. The composition as claimed in claim 1, wherein the disaccharide is maltose.

13. The composition as claimed in claim 1, wherein the polyol is sorbitol.

14. The composition as claimed in claim 1, wherein the total amount of disaccharide and of polyol contained in one effective dose of the vaccine composition is between 10 mg and 50 mg.

15. The composition as claimed in claim 1, in which the chelating agent is EDTA or an EDTA salt.

16. The composition as claimed in claim 1, wherein the amount of chelating agent contained in one effective dose of the vaccine composition is between 0.01 mg and 0.1 mg.

17. The composition as claimed in claim 1, wherein the amount of urea or of urea derivative contained in one effective dose of the vaccine composition is between 0.3 mg and 1.5 mg.

18. The composition as claimed in claim 1, wherein the nonionic surfactant is a poloxamer.

19. The composition as claimed in claim 1, wherein the poloxamer is poloxamer 188.

20. The composition as claimed in claim 1, wherein the amount of nonionic surfactant contained in one effective dose of the vaccine composition is between 0.001 mg and 0.5 mg.

21. The composition as claimed in claim 1, wherein the pH of the vaccine composition is between 7.0 and 9.0.

22. The composition as claimed in claim 1, wherein the buffer solution is a phosphate buffer, a Tris buffer, a HEPES buffer, or a mixture thereof.

23. The composition as claimed in claim 1, wherein the buffer solution comprises a phosphate buffer, the molarity of which is between 10 and 100 mM.

24. A process for preparing a vaccine composition containing a preparation of purified inactivated whole rabies virus, the process comprising:
    a) producing a whole rabies virus preparation by harvesting the supernatant of a virus infected cell culture,
    b) purifying then inactivating the whole virus preparation or, alternatively, inactivating and then purifying the whole virus preparation, and
    c) diluting the preparation of purified inactivated whole virus in a stabilizing excipient, the composition of said stabilizing excipient comprising:
        i) a buffer solution,
        ii) a mixture of essential and nonessential amino acids,
        iii) a disaccharide,
        iv) a polyol,
        v) a chelating agent,
        vi) urea or a urea derivative, and
        vii) a nonionic surfactant.

25. The process as claimed in claim 24, wherein the process is carried out without introducing any exogenous product of animal origin.

26. The process as claimed in claim 24, wherein the process further comprises dividing the vaccine composition into packaging devices and optionally freeze-drying vaccine composition into the packaging devices.

27. A freeze-dried vaccine composition containing a preparation of purified inactivated whole virus that is obtained according to the process of claim 26.

28. A stabilizing excipient composition for an inactivated whole rabies virus vaccine, wherein the composition comprises:
    i) a buffer solution,
    ii) a mixture of essential and nonessential amino acids,
    iii) a disaccharide,
    iv) a polyol,
    v) a chelating agent,
    vi) urea or a urea derivative, and
    vii) a nonionic surfactant.

29. The stabilizing excipient composition as claimed in claim 28, wherein the excipient is free of protein, or of protein and of peptide.

30. The stabilizing excipient composition as claimed in claim 29 that is free of product of animal origin.

31. The composition as claimed in claim 1, wherein the stabilizing excipient is free of protein, of peptide, and of oligopeptide.

32. The stabilizing excipient composition as claimed in claim 28, wherein the excipient is free of protein, of peptide, and of oligopeptide.

* * * * *